(12) United States Patent
Mitsui et al.

(10) Patent No.: US 8,088,518 B2
(45) Date of Patent: Jan. 3, 2012

(54) METHOD FOR PRODUCING LITHIUM DIFLUOROBIS (OXALATO) PHOSPHATE SOLUTION

(75) Inventors: Toshinori Mitsui, Ube (JP); Kaname Hatakenaka, Koshigaya (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 13/121,586

(22) PCT Filed: Dec. 14, 2009

(86) PCT No.: PCT/JP2009/070803
§ 371 (c)(1),
(2), (4) Date: Mar. 29, 2011

(87) PCT Pub. No.: WO2010/071097
PCT Pub. Date: Jun. 24, 2010

(65) Prior Publication Data
US 2011/0183219 A1    Jul. 28, 2011

(30) Foreign Application Priority Data
Dec. 16, 2008    (JP) .................................. 2008-319834

(51) Int. Cl.
*H01M 6/16*    (2006.01)
(52) U.S. Cl. ........ 429/342; 429/341; 429/200; 429/322; 429/324
(58) Field of Classification Search .................. 429/342, 429/341, 200, 322, 324
See application file for complete search history.

(56) References Cited

U.S. PATENT DOCUMENTS

| 6,693,212 | B1* | 2/2004 | Wietelmann et al. | ........... 558/73 |
| 6,783,896 | B2* | 8/2004 | Tsujioka et al. | ............. 429/306 |
| 6,849,752 | B2 | 2/2005 | Tsujioka et al. | |
| 2010/0323240 | A1* | 12/2010 | Tsujioka et al. | ............. 429/199 |

FOREIGN PATENT DOCUMENTS

| JP | 2003-137890 A | 5/2003 |
| JP | 3907446 B2 | 1/2007 |
| JP | 2008-288049 A | 11/2008 |
| JP | 2008-305574 A | 12/2008 |

OTHER PUBLICATIONS

JP 2008-305574 translation.*
JP 2008-288049 translation.*
International Search Report including partial English translation dated Jan. 26, 2010 and PCT/ISA/237 Form (Seven (7) pages).

* cited by examiner

*Primary Examiner* — Patrick Ryan
*Assistant Examiner* — Alex Usyatinsky
(74) *Attorney, Agent, or Firm* — Crowell & Moring LLP

(57) ABSTRACT

Disclosed is a method for producing a lithium difluorobis (oxalato)phosphate solution, which is characterized by that lithium hexafluorophosphate and oxalic acid are mixed together in a nonaqueous solvent, in a manner that the molar ratio of lithium hexafluorophosphate to oxalic acid falls within a range of 1:1.90 to 1:2.10, and furthermore silicon tetrachloride is added to this, in a manner that the molar ratio of lithium hexafluorophosphate to silicon tetrachloride falls within a range of 1:0.95 to 1:1.10, thereby conducting a reaction. The lithium difluorobis(oxalato)phosphate solution produced by this method has low contents of chlorine compounds and free acids. Therefore, it can become an additive that is effective for improving performance of nonaqueous electrolyte batteries.

3 Claims, No Drawings

METHOD FOR PRODUCING LITHIUM DIFLUOROBIS (OXALATO) PHOSPHATE SOLUTION

TECHNICAL FIELD

The present invention relates to a method for producing a lithium difluorobis(oxalato)phosphate solution, which is used as an additive for nonaqueous electrolyte batteries.

BACKGROUND OF THE INVENTION

Lithium difluorobis(oxalato)phosphate is used as an additive for nonaqueous electrolyte batteries, such as lithium ion batteries, lithium ion capacitors, etc. Furthermore, as a method for producing lithium difluorobis(oxalato)phosphate, there is known a method of reacting lithium hexafluorophosphate in an organic solvent in the presence of an reaction aid containing $SiCl_4$ (Patent Publication 1). In this method, it is difficult to purify the lithium difluorobis(oxalato)phosphate solution by crystallization. Therefore, it is extremely difficult to obtain a lithium difluorobis(oxalato)phosphate, in which chlorine compounds and free acids are little, which produce an adverse effect on battery characteristics of nonaqueous electrolyte batteries.

PRIOR ART PUBLICATION

Patent Publication

Patent Publication 1: Japanese Patent No. 3907446

SUMMARY OF THE INVENTION

It is an object of the present invention to provide a method for industrially producing a lithium difluorobis(oxalato)phosphate solution, which can become an effective additive of nonaqueous electrolyte batteries and contains little chlorine compounds and free acids, with a low cost.

As a result of an eager study in view of such a prior art problem, the present inventors have found a method capable of industrially producing a lithium difluorobis(oxalato)phosphate, in which chlorine compounds and free acids are little, with a low cost, by studying reaction conditions, thereby reaching the present invention.

The present invention provides a method (a first method) for producing a lithium difluorobis(oxalato)phosphate solution, which is characterized by that lithium hexafluorophosphate and oxalic acid are mixed together in a nonaqueous solvent, in a manner that the molar ratio of lithium hexafluorophosp hate to oxalic acid falls within a range of 1:1.90 to 1:2.10, and furthermore silicon tetrachloride is added to this, in a manner that the molar ratio of lithium hexafluorophosphate to silicon tetrachloride falls within a range of 1:0.95 to 1:1.10, thereby conducting a reaction.

The first method may be a method (a second method) for producing a lithium difluorobis(oxalato)phosphate, which is characterized by that temperature when conducting the reaction by adding silicon tetrachloride is a range of 30° C. to 50° C.

The first or second method may be a method (a third method) for producing a lithium difluorobis(oxalato)phosphate solution, which is characterized by that the nonaqueous solvent is at least one kind of solvent selected from the group consisting of cyclic carbonates, chain-like carbonates, cyclic esters, and chain-like esters.

DETAILED DESCRIPTION

It is possible by the present invention to industrially produce, with a low cost, a lithium difluorobis(oxalato)phosphate solution, which can become an additive that is effective for improving performance of nonaqueous electrolyte batteries.

In the following, the present invention is explained in more detail.

The method of the present invention for producing a lithium difluorobis(oxalato)phosphate solution is one characterized by that lithium hexafluorophosphate and oxalic acid are mixed together in a nonaqueous solvent, and furthermore silicon tetrachloride is added to this, thereby conducting a reaction.

As the oxalic acid used for the lithium difluorobis(oxalato)phosphate production of the present invention, it is possible to use one prepared by drying a commercial dihydrate. The drying method is not particularly limited, and it is possible to use a method such as heating, vacuum drying, etc. One having a water content of 300 mass ppm or less in the dried oxalic acid is preferable. If the water concentration exceeds 300 mass ppm, lithium hexafluorophosphate and lithium difluorobis(oxalato)phosphate are hydrolyzed. Therefore, it is not preferable.

The nonaqueous solvent used for the lithium difluorobis(oxalato)phosphate production of the present invention is, for example, at least one kind of solvent selected from the group consisting of cyclic carbonates, chain-like carbonates, cyclic esters, and chain-like esters. As concrete examples, it is possible to cite cyclic carbonates such as propylene carbonate, ethylene carbonate and butylene carbonate, chain-like carbonates such as diethyl carbonate, dimethyl carbonate and ethyl methyl carbonate, cyclic esters such as γ-butyrolactone and γ-valerolactone, and chain-like esters such as methyl acetate and methyl propionate. As these solvents, it is preferable to use dehydrated ones. The dehydration method is not particularly limited. For example, it is possible to use a method of adsorbing water by synthetic zeolite, etc. The water concentration in the nonaqueous solvent used in the present invention is preferably 100 mass ppm or less. If the water concentration exceeds 100 mass ppm, lithium hexafluorophosphate and lithium difluorobis(oxalato)phosphate are hydrolyzed. Therefore, it is not preferable. Furthermore, as the nonaqueous solvent used in the present invention, it is possible to use one kind alone or to use at least two kinds in accordance with use by mixing them with an arbitrary combination and an arbitrary proportion.

The concentration of lithium hexafluorophosphate in the nonaqueous solvent used in the present invention can be set at an arbitrary concentration with no particular limitation. It is a range in which the lower limit is preferably 1%, more preferably 5% and in which the upper limit is preferably 35%, more preferably 30%. If it is lower than 1%, the lithium difluorobis(oxalato)phosphate solution to be obtained is dilute. Therefore, it is necessary to have concentration for a long time to be used as an electrolyte of nonaqueous electrolyte batteries. Thus, it is not economical. On the other hand, if it is greater than 35%, it is difficult to smoothly conduct the reaction, since viscosity of the solution increases. Therefore, it is not preferable.

The molar ratio upon mixing together lithium hexafluorophosphate and oxalic acid is preferably in a range of 1:1.90 to 1:2.10, more preferably in a range of 1:1.95 to 1:2.05. If the amount of oxalic acid is less than 1.90 moles relative to 1 mole of lithium hexafluorophosphate, a lot of nonvolatile chlorine compounds are produced as by-products. Therefore, it becomes difficult to be used as an additive of nonaqueous electrolyte batteries. If the amount of oxalic acid is greater than 2.10 moles relative to 1 mole of lithium hexafluorophosphate, the free acid concentration becomes high. Therefore, it becomes difficult to be used as an additive of nonaqueous electrolyte batteries.

It is preferable to conduct the reaction by adding silicon tetrachloride in a manner that the molar ratio of lithium hexafluorophosphate to silicon tetrachloride falls in a range of 1:0.95 to 1:10. More preferably, it is preferable to conduct the reaction by adding that in a manner that the molar ratio is in a range of 1:1.00 to 1:1.05. If the addition of silicon tetrachloride is less than 0.95 moles relative to 1 mole of lithium hexafluorophosphate, a lot of lithium tetrafluoro(oxalato)phosphate is contained as an intermediate product, thereby lowering purity of lithium difluorobis(oxalato)phosphate. Thus, it is not preferable. If the addition of silicon tetrachloride is greater than 1.10 moles relative to 1 mole of lithium hexafluorophosphate, a lot of nonvolatile chlorine compounds are produced as by-products. Thus, it becomes difficult to use that as an additive of nonaqueous electrolyte batteries.

The temperature upon conducting the reaction by adding silicon tetrachloride is preferably a range of 30° C. to 50° C. More preferably, it is a range of 35° C. to 45° C. If the temperature upon conducting the reaction exceeds 50° C., the chlorine compounds concentration in the obtained solution increases. Therefore, it becomes difficult to use that as an additive of nonaqueous electrolyte batteries. Furthermore, if it exceeds 50° C., the amount of volatilization of silicon tetrachloride is large. Thus, it is not preferable. If the temperature upon conducting the reaction is lower than 30° C., reactivity lowers. Therefore, it is necessary to prolong the reaction time, and that is not economical.

The method for adding silicon tetrachloride is not particularly limited. It may be conducted under an arbitrary condition suitable for the condition. For example, it is possible to cite a method of pumping that by using an inert gas, a method of introducing that by using a metering pump, etc.

The time for the addition of silicon tetrachloride is not particularly limited. It can be an arbitrary time, but it is preferable to conduct the addition by spending 1 to 10 hours. If the time for the addition is shorter than 1 hour, the amount of silicon tetrachloride that volatilizes under the unreacted condition is high. Thus, it is not preferable. If the introduction time is longer than 10 hours, it is not economical since it requires a long time. After terminating the addition of silicon tetrachloride, it is preferable to conduct the reaction by a further maintenance for about one hour to three hours.

In this reaction, lithium difluorobis(oxalato)phosphate as the product is subjected to hydrolysis by water. Therefore, it is preferable to conduct the reaction in an atmosphere containing no water. For example, it is preferable to conduct the reaction in an atmosphere of an inert gas such as nitrogen.

It is possible to remove HCl, $SiF_4$ or $SiCl_4$, which is contained in the lithium difluorobis(oxalato)phosphate solution obtained by the reaction, by depressurizing the reactor. By conducting a filtration after the depressurizing treatment, it is possible to remove insoluble substances.

The lithium difluorobis(oxalato)phosphate solution obtained after the depressurizing treatment and the filtration contains chlorine compounds, free acids or lithium tetrafluoro(oxalato)phosphate, which are not removed by the depressurizing treatment and the filtration. It is possible to obtain a lithium difluorobis(oxalato)phosphate solution, which is little in chlorine compounds and free acids, for example, which has in terms of chlorine compounds a chlorine concentration of about 5 mass ppm or less per 1 mass % of lithium difluorobis(oxalato)phosphate, and which has in terms of free acids an acid concentration of about 250 mass ppm or less converted into hydrofluoric acid. In case that the chlorine concentration is higher than 5 mass ppm or that the acid concentration is higher than 250 mass ppm, it is difficult to use that as an additive of nonaqueous electrolyte batteries.

A preparation method for using a lithium difluorobis(oxalato)phosphate solution obtained by the present invention, as an electrolyte for nonaqueous electrolyte batteries is not particularly limited. It is possible to obtain a desired electrolyte for nonaqueous electrolyte batteries by adding the above-mentioned nonaqueous solvent, a main electrolyte or other additives to the lithium difluorobis(oxalato)phosphate solution obtained by the production method of the present invention, to have predetermined concentrations.

As the main electrolyte to be added, it is possible to cite electrolytic lithium salts represented by $LiPF_6$, $LiBF_4$, $LiClO_4$, $LiAsF_6$, $LiSbF_6$, $LiCF_3SO_3$, $LiN(SO_2CF_3)_2$, $LiN(SO_2C_2F_6)_2$, $LiN(SO_2CF_3)(SO_2C_4F_6)$, $LiC(SO_2CF_3)_3$, $LiPF_3(C_3F_7)_3$, $LiB(CF_3)_4$, $LiBF_3(C_2F_5)$, etc.

Furthermore, as other additives to be added, it is possible to cite compounds having the overcharge preventive effect, the anode film forming effect and the cathode protective effect, such as lithium tetrafluoro(oxalato)phosphate, lithium difluoro(oxalato)borate, cyclohexyl benzene, biphenyl, t-butylbenzene, vinylene carbonate, vinylethylene carbonate, difluoroanisole, fluoroethylene carbonate, propane sultone, and dimethylvinylene carbonate.

In the following, the present invention is concretely explained by examples, but the present invention is not limited by such examples.

EXAMPLE 1

In a glove box of a dew point of −50° C., a 1000 ml three-necked flask was charged with 460 g of diethyl carbonate dehydrated to a water content of 10 mass ppm, followed by putting a stirring bar therein. With a sufficient stirring by a magnetic stirrer, 75.9 g of lithium hexafluorophosphate was added and dissolved. There was added 90.0 g of oxalic acid dried to a water content of 150 mass ppm. The molar ratio of lithium hexafluorophosphate to oxalic acid is 1.00:2.00. The three-necked flask was taken out of the glove box and immersed in a water bath set at 40° C. A magnetic stirrer was installed under the water bath, and a sufficient stirring was conducted.

Next, 87.5 g of silicon tetrachloride was put into a flask equipped with a cock, followed by attaching a septum to the mouth. The molar ratio of lithium hexafluorophosphate to silicon tetrachloride is 1.00:1.03. By inserting a cannula into the septum and then turning the cock to introduce nitrogen gas, silicon tetrachloride was pumped into a mixed liquid of lithium hexafluorophosphate, oxalic acid and diethyl carbonate by using the cannula to conduct a dropping by spending one hour. At the same time as the dropping was started, $SiF_4$ and HCl gases were generated. The generated gases were allowed to flow into a can filled with soda lime and absorbed. The undissolved oxalic acid was dissolved, and the reaction was allowed to proceed. After terminating the addition, the stirring was continued for one hour, and the reaction was terminated.

Diethyl carbonate was distilled out of the obtained reaction liquid at 50° C. under a vacuum condition of 133 Pa. Then, the three-necked flask was put into the glove box, and the diethyl carbonate solution was filtrated by a membrane filter. Several drops of the filtrate were taken into an NMR tube, followed by adding an internal standard, dissolving it by adding acetonitrile-d3, and then conducting NMR measurement. From the integration ratio of NMR, the content by percentage contained in the filtrate was calculated. It contained 34 mass % of lithium difluorobis(oxalato)phosphate and 3 mass % of lithium tetrafluoro(oxalato)phosphate. Yield of lithium difluorobis(oxalato)phosphate was 84%, based on the feed amount of lithium hexafluorophosphate.

To measure the contained chlorine compound concentration, fluorescence X-ray measurement was conducted. The chlorine concentration in the sample was determined. As the chlorine concentration in this sample was divided by the lithium difluorobis(oxalato)phosphate concentration to convert it per 1 mass %, it became 0.7 mass ppm.

The concentration of acids contained was measured by titration method. As the acid concentration was divided by the lithium difluorobis(oxalato)phosphate to convert it per 1 mass %, it was found to be 90 mass ppm in terms of hydrofluoric acid.

EXAMPLE 2

The synthesis was conducted in the same manner as that of Example 1, except in that 93.6 g of oxalic acid was used and that the molar ratio of lithium hexafluorophosphate to oxalic acid was set at 1.00:2.08. The NMR measurement was conducted in the same manner as that of Example 1. From the integration ratio of NMR, the content by percentage contained in the filtrate was calculated. It contained 33 mass % of lithium difluorobis(oxalato)phosphate and 2 mass % of lithium tetrafluoro(oxalato)phosphate. Yield of lithium difluorobis(oxalato)phosphate was 84%, based on the feed amount of lithium hexafluorophosphate. The concentration of chlorine in this sample was measured in the same method as that of Example 1. As it was divided by the lithium difluorobis(oxalato)phosphate concentration to convert it per 1 mass %, it became 0.7 mass ppm. As the acid concentration was examined by titration, it was found to be 105 mass ppm in terms of hydrofluoric acid.

EXAMPLE 3

The synthesis was conducted in the same manner as that of Example 1, except in that 86.4 g of oxalic acid was used and that the molar ratio of lithium hexafluorophosphate to oxalic acid was set at 1.00:1.92. The NMR measurement was conducted in the same manner as that of Example 1. From the integration ratio of NMR, the content by percentage contained in the filtrate was calculated. It contained 31 mass % of lithium difluorobis(oxalato)phosphate and 4 mass % of lithium tetrafluoro(oxalato)phosphate. Yield of lithium difluorobis(oxalato)phosphate was 77%, based on the feed amount of lithium hexafluorophosphate. The concentration of chlorine in this sample was measured in the same method as that of Example 1. As it was divided by the lithium difluorobis(oxalato)phosphate concentration to convert it per 1 mass %, it became 1.4 mass ppm. As the acid concentration was examined by titration, it was found to be 50 mass ppm in terms of hydrofluoric acid.

EXAMPLE 4

The synthesis was conducted in the same manner as that of Example 1, except in that 91.7 g of silicon tetrachloride was used and that the molar ratio of lithium hexafluorophosphate to silicon tetrachloride was set at 1.00:1.08. The NMR measurement was conducted in the same manner as that of Example 1. From the integration ratio of NMR, the content by percentage contained in the filtrate was calculated. It contained 33 mass % of lithium difluorobis(oxalato)phosphate and 1 mass % of lithium tetrafluoro(oxalato)phosphate. Yield of lithium difluorobis(oxalato)phosphate was 83%, based on the feed amount of lithium hexafluorophosphate. The concentration of chlorine in this sample was measured in the same method as that of Example 1. As it was divided by the lithium difluorobis(oxalato)phosphate concentration to convert it per 1 mass %, it became 1.1 mass ppm. As the acid concentration was examined by titration, it was found to be 70 mass ppm in terms of hydrofluoric acid.

EXAMPLE 5

The synthesis was conducted in the same manner as that of Example 1, except in that 82.4 g of silicon tetrachloride was used and that the molar ratio of lithium hexafluorophosphate to silicon tetrachloride was set at 1.00:0.97. The NMR measurement was conducted in the same manner as that of Example 1. From the integration ratio of NMR, the content by percentage contained in the filtrate was calculated. It contained 30 mass % of lithium difluorobis(oxalato)phosphate and 5 mass % of lithium tetrafluoro(oxalato)phosphate. Yield of lithium difluorobis(oxalato)phosphate was 76%, based on the feed amount of lithium hexafluorophosphate. The concentration of chlorine in this sample was measured in the same method as that of Example 1. As it was divided by the lithium difluorobis(oxalato)phosphate concentration to convert it per 1 mass %, it became 0.8 mass ppm. As the acid concentration was examined by titration, it was found to be 120 mass ppm in terms of hydrofluoric acid.

EXAMPLE 6

The synthesis was conducted in the same manner as that of Example 1, except in that the reaction temperature was set at 25° C., but reactivity was low. Therefore, the reaction was conducted for 24 hours after adding silicon tetrachloride. The NMR measurement was conducted in the same manner as that of Example 1. From the integration ratio of NMR, the content by percentage contained in the filtrate was calculated. It contained 32 mass % of lithium difluorobis(oxalato)phosphate and 4 mass % of lithium tetrafluoro(oxalato)phosphate. Yield of lithium difluorobis(oxalato)phosphate was 75%, based on the feed amount of lithium hexafluorophosphate. The concentration of chlorine in this sample was measured in the same method as that of Example 1. As it was divided by the lithium difluorobis(oxalato)phosphate concentration to convert it per 1 mass %, it became 0.9 mass ppm. As the acid concentration was examined by titration, it was found to be 200 mass ppm in terms of hydrofluoric acid.

EXAMPLE 7

The synthesis was conducted in the same manner as that of Example 1, except in that the reaction temperature was set at 60° C. The NMR measurement was conducted in the same manner as that of Example 1. From the integration ratio of NMR, the content by percentage contained in the filtrate was calculated. It contained 31 mass % of lithium difluorobis(oxalato)phosphate and 2 mass % of lithium tetrafluoro(oxalato)phosphate. Yield of lithium difluorobis(oxalato)phosphate was 77%, based on the feed amount of lithium hexafluorophosphate. The concentration of chlorine in this sample was measured in the same method as that of Example 1. As it was divided by the lithium difluorobis(oxalato)phosphate concentration to convert it per 1 mass %, it became 4.1 mass ppm. As the acid concentration was examined by titration, it was found to be 90 mass ppm in terms of hydrofluoric acid.

EXAMPLE 8

In a glove box of a dew point of −50° C., a 1000 ml three-necked flask was charged with 425 g of ethyl methyl carbonate dehydrated to a water content of 10 mass ppm, followed by putting a stirring bar therein. With a sufficient stirring by a magnetic stirrer, 106.3 g of lithium hexafluorophosphate was added and dissolved. There was added 126.1 g of oxalic acid dried to a water content of 150 mass ppm. The molar ratio of lithium hexafluorophosphate to oxalic acid is 1.00:2.00. The three-necked flask was taken out of the glove box and immersed in a water bath set at 40° C. A magnetic stirrer was installed under the water bath, and a sufficient stirring was conducted.

Next, 123.7 g of silicon tetrachloride was put into a flask equipped with a cock, followed by attaching a septum to the mouth. The molar ratio of lithium hexafluorophosphate to silicon tetrachloride is 1.00:1.04. By inserting a cannula into the septum and then turning the cock to introduce nitrogen gas, silicon tetrachloride was pumped into a mixed liquid of lithium hexafluorophosphate, oxalic acid and ethyl methyl carbonate by using the cannula to conduct a dropping by spending one hour. At the same time as the dropping was started, $SiF_4$ and HCl gases were generated. The generated gases were allowed to flow into a can filled with soda lime and absorbed. The undissolved oxalic acid was dissolved, and the reaction was allowed to proceed. After terminating the addition, the stirring was continued for one hour, and the reaction was terminated.

Ethyl methyl carbonate was distilled out of the obtained reaction liquid at 50° C. under a vacuum condition of 133 Pa. Then, the three-necked flask was put into the glove box, and the ethyl methyl carbonate solution was filtrated by a membrane filter. Several drops of the filtrate were taken into an NMR tube, followed by adding an internal standard, dissolving it by adding acetonitrile-d3, and then conducting NMR measurement. From the integration ratio of NMR, the content by percentage contained in the filtrate was calculated. It contained 37 mass % of lithium difluorobis(oxalato)phosphate and 2 mass % of lithium tetrafluoro(oxalato)phosphate. Yield of lithium difluorobis(oxalato)phosphate was 85%, based on the feed amount of lithium hexafluorophosphate.

To measure the contained chlorine compound concentration, fluorescence X-ray measurement was conducted. The chlorine concentration in the sample was determined. As the chlorine concentration in this sample was divided by the lithium difluorobis(oxalato)phosphate concentration to convert it per 1 mass %, it became 0.7 mass ppm.

The concentration of acids contained was measured by titration method. As the acid concentration was divided by the lithium difluorobis(oxalato)phosphate to convert it per 1 mass %, it was found to be 90 mass ppm in terms of hydrofluoric acid.

COMPARATIVE EXAMPLE 1

The synthesis was conducted in the same manner as that of Example 1, except in that 98.6 g of oxalic acid was used and that the molar ratio of lithium hexafluorophosphate to oxalic acid was set at 1.00:2.19. The NMR measurement was conducted in the same manner as that of Example 1. From the integration ratio of NMR, the content by percentage contained in the filtrate was calculated. It contained 33 mass % of lithium difluorobis(oxalato)phosphate and 3 mass % of lithium tetrafluoro(oxalato)phosphate. Yield of lithium difluorobis(oxalato)phosphate was 81%, based on the feed amount of lithium hexafluorophosphate. The concentration of chlorine in this sample was measured in the same method as that of Example 1. As it was divided by the lithium difluorobis(oxalato)phosphate concentration to convert it per 1 mass %, it became 0.8 mass ppm. As the acid concentration was examined by titration, it was found to be 500 mass ppm in terms of hydrofluoric acid.

COMPARATIVE EXAMPLE 2

The synthesis was conducted in the same manner as that of Example 1, except in that 99.4 g of silicon tetrachloride was used and that the molar ratio of lithium hexafluorophosphate to silicon tetrachloride was set at 1.00:1.17. The NMR measurement was conducted in the same manner as that of Example 1. From the integration ratio of NMR, the content by percentage contained in the filtrate was calculated. It contained 33 mass % of lithium difluorobis(oxalato)phosphate and 0.5 mass % of lithium tetrafluoro(oxalato)phosphate. Yield of lithium difluorobis(oxalato)phosphate was 80%, based on the feed amount of lithium hexafluorophosphate. The concentration of chlorine in this sample was measured in the same method as that of Example 1. As it was divided by the lithium difluorobis(oxalato)phosphate concentration to convert it per 1 mass %, it became 80 mass ppm. As the acid concentration was examined by titration, it was found to be 5 mass ppm in terms of hydrofluoric acid.

COMPARATIVE EXAMPLE 3

The synthesis was conducted in the same manner as that of Example 1, except in that 81.5 g of oxalic acid was used and that the molar ratio of lithium hexafluorophosphate to oxalic acid was set at 1.00:1.81. The NMR measurement was conducted in the same manner as that of Example 1. From the integration ratio of NMR, the content by percentage contained in the filtrate was calculated. It contained 28 mass % of lithium difluorobis(oxalato)phosphate and 8 mass % of lithium tetrafluoro(oxalato)phosphate. Yield of lithium difluorobis(oxalato)phosphate was 71%, based on the feed amount of lithium hexafluorophosphate. The concentration of chlorine in this sample was measured in the same method as that of Example 1. As it was divided by the lithium difluorobis(oxalato)phosphate concentration to convert it per 1 mass %, it became 70 mass ppm. As the acid concentration was examined by titration, it was found to be 10 mass ppm in terms of hydrofluoric acid.

COMPARATIVE EXAMPLE 4

The synthesis was conducted in the same manner as that of Example 1, except in that 73.9 g of silicon tetrachloride was used and that the molar ratio of lithium hexafluorophosphate to silicon tetrachloride was set at 1.00:0.87. The NMR measurement was conducted in the same manner as that of Example 1. From the integration ratio of NMR, the content by percentage contained in the filtrate was calculated. It contained 25 mass % of lithium difluorobis(oxalato)phosphate and 11 mass % of lithium tetrafluoro(oxalato)phosphate. Yield of lithium difluorobis(oxalato)phosphate was 60%, based on the feed amount of lithium hexafluorophosphate. The concentration of chlorine in this sample was measured in the same method as that of Example 1. As it was divided by the lithium difluorobis(oxalato)phosphate concentration to convert it per 1 mass %, it became 0.9 mass ppm. As the acid concentration was examined by titration, it was found to be 450 mass ppm in terms of hydrofluoric acid.

The invention claimed is:

1. A method for producing a lithium difluorobis(oxalato) phosphate solution, comprising the steps of:
    (a) mixing lithium hexafluorophosphate and oxalic acid together in a nonaqueous solvent, in a manner that molar ratio of lithium hexafluorophosphate to oxalic acid falls within a range of 1:1.90 to 1:2.10, to prepare a mixture; and
    (b) adding silicon tetrachloride to the mixture, in a manner that molar ratio of lithium hexafluorophosphate to silicon tetrachloride falls within a range of 1:0.95 to 1:1.10, thereby conducting a reaction.

2. A method for producing a lithium difluorobis(oxalato) phosphate solution according to claim 1, wherein temperature for conducting the step (b) is in a range of 30° C. to 50° C.

3. A method for producing a lithium difluorobis(oxalato) phosphate solution according to claim 1, wherein the nonaqueous solvent is at least one kind of solvent selected from the group consisting of cyclic carbonates, chain-like carbonates, cyclic esters, and chain-like esters.

* * * * *